(12) United States Patent
Eckert

(10) Patent No.: US 7,678,314 B1
(45) Date of Patent: Mar. 16, 2010

(54) PROPHYLAXIS CUP HAVING PERLITE PARTICLES, METHODS OF FORMING AND METHOD OF USE

(76) Inventor: Ronald C. Eckert, 4267 Sugar Maple La., Okemos, MI (US) 48864

(*) Notice: Subject to any disclaimer, the term of this patent is extended or adjusted under 35 U.S.C. 154(b) by 591 days.

(21) Appl. No.: 10/877,277

(22) Filed: Jun. 25, 2004

Related U.S. Application Data

(60) Provisional application No. 60/482,550, filed on Jun. 25, 2003.

(51) Int. Cl.
  *B29C 37/02* (2006.01)
  *B29C 43/36* (2006.01)
(52) U.S. Cl. .................. 264/161; 264/162; 264/236; 264/299; 264/331.11
(58) Field of Classification Search ............ 264/331.11
  See application file for complete search history.

(56) References Cited

U.S. PATENT DOCUMENTS

| | | | |
|---|---|---|---|
| 3,964,166 A * | 6/1976 | Stahlman | 433/166 |
| 4,116,919 A * | 9/1978 | Elias et al. | 523/213 |
| 4,627,197 A * | 12/1986 | Klee et al. | 451/3 |
| 4,793,103 A * | 12/1988 | Baumgart | 451/81 |
| 4,906,464 A * | 3/1990 | Yamamoto et al. | 424/489 |
| 5,164,461 A * | 11/1992 | Mitchell et al. | 525/478 |
| 5,334,020 A | 8/1994 | Eckert | |
| 6,432,387 B1 * | 8/2002 | Kaizuka | 424/49 |
| 2003/0084534 A1 | 5/2003 | Kaizuka | |
| 2003/0203337 A1 | 10/2003 | Roulston et al. | |
| 2003/0224702 A1 | 12/2003 | Roulston et al. | |
| 2004/0074031 A1 | 4/2004 | Davies et al. | |
| 2005/0281760 A1 * | 12/2005 | Overoyen | 424/58 |

OTHER PUBLICATIONS

Advances in Abrasive Technology in Prophylaxis Pastes, Compendium of Continuing Education in Dentistry, vol. 23: 1 (2002), pp. 61-70.

\* cited by examiner

*Primary Examiner*—Monica A Huson
(74) *Attorney, Agent, or Firm*—Ian C. McLeod

(57) ABSTRACT

A prophylaxis cup formed of a silicone elastomer having perlite particles incorporated therein as an abrasive material. The silicone elastomer and perlite particles are processed in a 3-roll mill so that the perlite particles have a predetermined size and are uniformly dispersed throughout the prophylaxis cup. As the prophylaxis cup is used to clean and polish teeth, the prophylaxis cup disintegrates upon contact with the teeth releasing the perlite particles which act as a cleaning and polishing agent between the prophylaxis cup and the teeth.

9 Claims, 3 Drawing Sheets

PROPHYLAXIS CUP HAVING PERLITE PARTICLES, METHODS OF FORMING AND METHOD OF USE

CROSS-REFERENCE TO RELATED APPLICATION

This application claims the benefit of U.S. Provisional Application Ser. No. 60/482,550, filed Jun. 25, 2003.

STATEMENT REGARDING FEDERALLY SPONSORED RESEARCH OR DEVELOPMENT

Not Applicable

BACKGROUND OF THE INVENTION (1) Field of the Invention

The present invention relates to a disposable prophylaxis cup formed of a silicone elastomer having perlite particles incorporated therein. The present invention also relates to a method of forming a prophylaxis cup of a silicone elastomer having perlite particles uniformly distributed throughout. In addition, the present invention relates to a method of using a prophylaxis cup formed of a silicone elastomer having perlite particles to clean and polish teeth.

(2) Description of the Related Art

The related art has described disposable prophylaxis cups formed of a silicone elastomer incorporated with pumice material as an abrasive for use in cleaning teeth. Illustrative is U.S. Pat. No. 5,334,020 to Eckert.

The related art has also described the use of perlite in various dental tools as an abrasive material for cleaning teeth. Perlite is a naturally occurring siliceous rock. In particular, U.S. Patent Application Publication 2003/0084534 A1 to Kaizuka describes a toothbrush with bristles containing a far-infrared emitting material and multi-element minerals. One of the multi-element minerals is perlite. In addition, U.S. Patent Application Publication 2004/0074031 A1 to Davies et al. describes a toothbrush having a resilient element for whitening and polishing the teeth. The resilient element is constructed of an elastomer into which is incorporated perlite. The perlite can be crude or non-expanded perlite but is preferably expanded perlite.

Also of interest are U.S. Patent Application Publication Nos. 2003/0224702 A1 and 2003/0203337 A1 both to Roulston which describe a polishing composition using unexpanded perlite ore and methods of using the polishing composition such as to polish teeth.

It is also known in the art to use perlite in prophylaxis pastes for cleaning and polishing teeth as shown in the article entitled "Advances in Abrasive Technology in Prophylaxis Pastes", Compendium of Continuing Education in Dentistry, Vol. 23: 1 (2002), pp. 61-70. 3M ESPE Dental Products of St. Paul, Minn. manufactures a paste having perlite under the trademark ClinPro™ Prophy.

Finally, it is known in the art to use either a 2-roll mill or a low intensity type mixer such as a 1-arm or a 2-arm mixer to mix the abrasives into the silicone elastomer to form the compound for the prophylaxis cup. This method has worked in the past since previously the abrasives used in the prophylaxis cups were discrete particles with no tendency to agglomerate. However, the use of perlite as the abrasive has necessitated a change in the method of forming the prophylaxis cups.

Thus, there remains a need for a disposable prophylaxis cup and for a method for forming the prophylaxis cup where perlite particles are incorporated into the prophylaxis cup and where the prophylaxis cup when rotating, disintegrated under load upon contact with the teeth to release the perlite particles to clean and polish the teeth.

SUMMARY OF THE INVENTION

A prophylaxis cup formed of a silicone elastomer having perlite particles incorporated therein as an abrasive material. To form the prophylaxis cup, the silicone and perlite particles are mixed together to form a compound. In one (1) embodiment, the perlite particles make up between about 30 and 36 percent by weight of the compound used to form the prophylaxis cup. The compound having the silicone and perlite particles is passed through a 3-roll mill so that the perlite particles are reduced to a predetermined size and are evenly or uniformly distributed throughout the prophylaxis cup. Next, the compound is placed in a preheated mold and molded under heat and pressure. The prophylaxis cup is then removed from the mold and is post-cured. Finally, the prophylaxis cup is cryogenically deflashed by bombarding the prophylaxis cup with plastic bb's. The deflashing alters the surface of the prophylaxis cup so that the prophylaxis cup begins to disintegrate more quickly during use upon contact with the teeth.

The disposable prophylaxis cup is used to clean and polish the teeth. First, the prophylaxis cup is removably mounted on a prophylaxis angle and the prophylaxis angle is activated to rotate the prophylaxis cup. Next, the prophylaxis cup is positioned on the teeth so that the axis of the cup is perpendicular to the surface of the tooth. The prophylaxis cup is moved along the patient's teeth from tooth to tooth. As the prophylaxis cup is moved along the patient's teeth, the rotational contact of the prophylaxis cup with the teeth under load causes the prophylaxis cup to disintegrate. As the prophylaxis cup disintegrates, the perlite particles are separated from the prophylaxis cup. The perlite particles and the moisture on the teeth form a slurry between the prophylaxis cup and the teeth. As the prophylaxis cup is moved along the teeth, the slurry acts as a cleaning and polishing agent and removes stains from the teeth. The perlite particles in the slurry continue to contact the teeth and break down into smaller perlite particles. The smaller perlite particles act as a polishing agent for the final stage of the polishing procedure.

The present invention relates to a disposable prophylaxis cup for cleaning and polishing teeth, which comprises: a silicone elastomer; and perlite particles incorporated in the silicone elastomer as an abrasive material.

Further, the present invention relates to a method for cleaning and polishing teeth, which comprises the steps of: providing a disposable prophylaxis cup including a silicone elastomer having perlite particles as an abrasive material incorporated therein; providing a prophylaxis angle; mounting the prophylaxis cup on the prophylaxis angle; positioning the prophylaxis cup adjacent the teeth; activating the prophylaxis angle such that the prophylaxis cup rotates; moving the prophylaxis cup into contact with the teeth wherein the prophylaxis cup begins to disintegrate and the perlite particles in the prophylaxis cup are gradually separated from the prophylaxis cup so that a slurry having the perlite particles is formed between the teeth and the prophylaxis cup; and moving the prophylaxis cup along the teeth wherein the slurry between the prophylaxis cup and the teeth acts as a cleaning and polishing agent to clean and polish the teeth as the prophylaxis cup is moved along the teeth.

Still further, the present invention relates to a method for forming a prophylaxis cup which comprises the steps of: providing a silicone elastomer; providing perlite particles;

mixing the silicone elastomer and the perlite particles so that the perlite particles are evenly dispersed into the silicone elastomer to produce a compound; providing a 3-roll mill; passing the compound through the 3-roll mill at least twice to achieve separation of any agglomerated perlite particles and to produce uniform dispersion of the perlite particles in the silicone elastomer; loading the compound into the mold and closing the mold around the compound; removing the prophylaxis cup from the mold; post curing the prophylaxis cup; and deflashing the prophylaxis cup using a cryogenic deflashing system.

The substance and advantages of the present invention will become increasingly apparent by reference to the following drawings and the description.

BRIEF DESCRIPTION OF THE PREFERRED EMBODIMENTS

Figure 1:
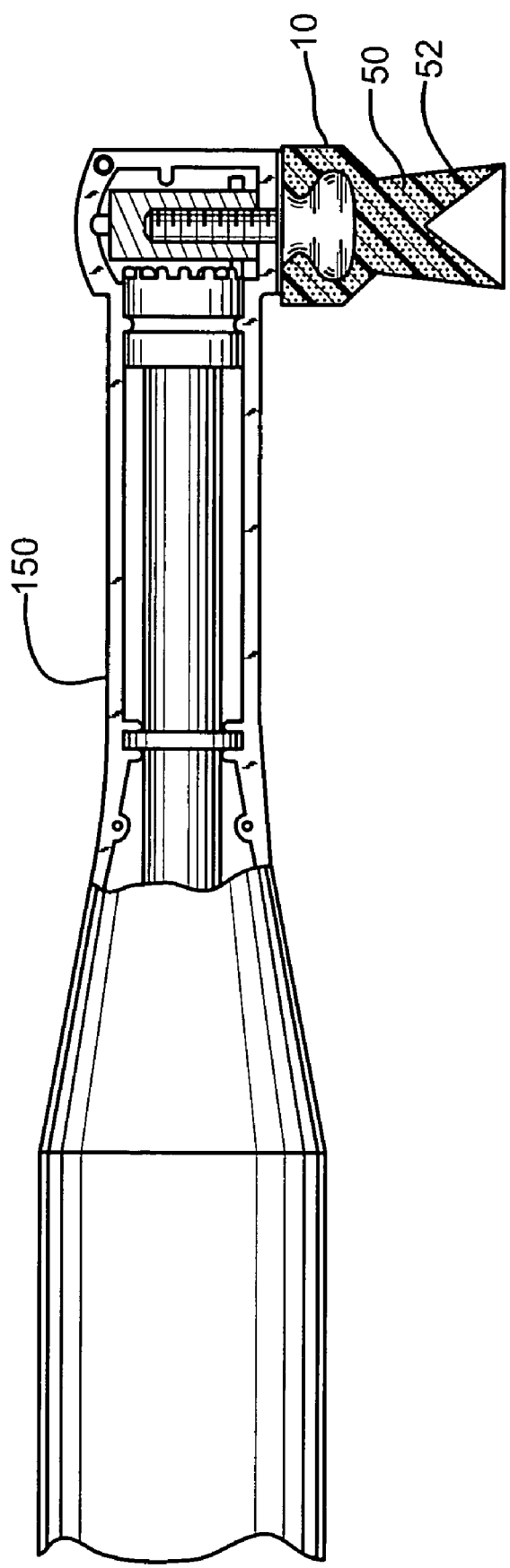
FIG. 1 is a cross-sectional side view of the prophylaxis cup 10 of the present invention mounted on a prophylaxis angle 150.

FIG. 1 shows the flexible prophylaxis cup 10 of the present invention used for cleaning and polishing teeth 20. The prophylaxis cup 10 is constructed of a compound having a silicone elastomer material 50 to enable the prophylaxis cup 10 to be flexible and perlite particles 52 to provide the abrasion necessary to clean and polish the teeth 20. The perlite particles 52 in the prophylaxis cup 10 enable the prophylaxis cup 10 to be used on teeth 20 to remove stains and to produce a high polish. Since the prophylaxis cup 10 incorporates an abrasive material distributed evenly throughout, there is no need to use a dental paste in combination with the prophylaxis cup 10. One (1) of the benefits of using perlite is that perlite is significantly less abrasive than any other abrasives used for teeth cleaning. The prophylaxis cup 10 of the present invention is particularly effective for use in pediatric dental care. In one (1) embodiment, the silicone elastomer material 50 is platinum cured methyl vinyl siloxane and the perlite particles 52 are Grade FA expanded perlite.

To produce the prophylaxis cups 10, the silicone elastomer 50 and the perlite particles 52 must be mixed together into a compound. Before the silicone elastomer 50 and the perlite particles 52 are mixed together to form the compound, the silicone elastomer 50 and the perlite particles 52 are weighed using a triple beam balance or equivalent scales to achieve the correct formulation. In one (1) embodiment, the perlite particles 52 make up between about 30 and 36 percent by weight of the compound used to form the prophylaxis cup 10. Testing of compounds having varying percentages by weight of perlite particles 52, found that a prophylaxis cup 10 produced with a compound having less than 20 percent by weight of perlite particles 52 maintained its integrity during use but did not successfully polish or clean teeth 20. A prophylaxis cup 10 formed from a compound having approximately 20 percent by weight of perlite particles 52 maintained its integrity while removing plaque and mild or light stains as well as polishing the teeth 20. It was found that a prophylaxis cup 10 formed from a compound having between about 20 to 25 percent by weight of perlite particles 52 was successful for cleaning and polishing children's teeth. A prophylaxis cup 10 produced from a compound having between approximately 25 and 28 percent by weight of perlite particles 52 maintained its integrity and removed plaque and moderate stains as well as polishing the teeth 20. A prophylaxis cup 10 produced from a compound having approximately 33 percent by weight of perlite particles 52 removed plaque as well as heavy stains and also polished teeth 20. A prophylaxis cup 10 having 36 percent or greater by weight of perlite particles 52 disintegrated too rapidly during use and was unable to complete a standard prophylaxis procedure. It is understood that the prophylaxis cup 10 will wear down or disintegrate during normal use. To be successful, the prophylaxis cup 10 must be able to complete a standard dental prophylaxis procedure without disintegrating to the point that the prophylaxis cup 10 can no longer be used. A single prophylaxis cup 10 is disposable and intended for single use. A single prophylaxis cleaning and polishing procedure normally takes between about 4 and 15 minutes.

Figure 3:
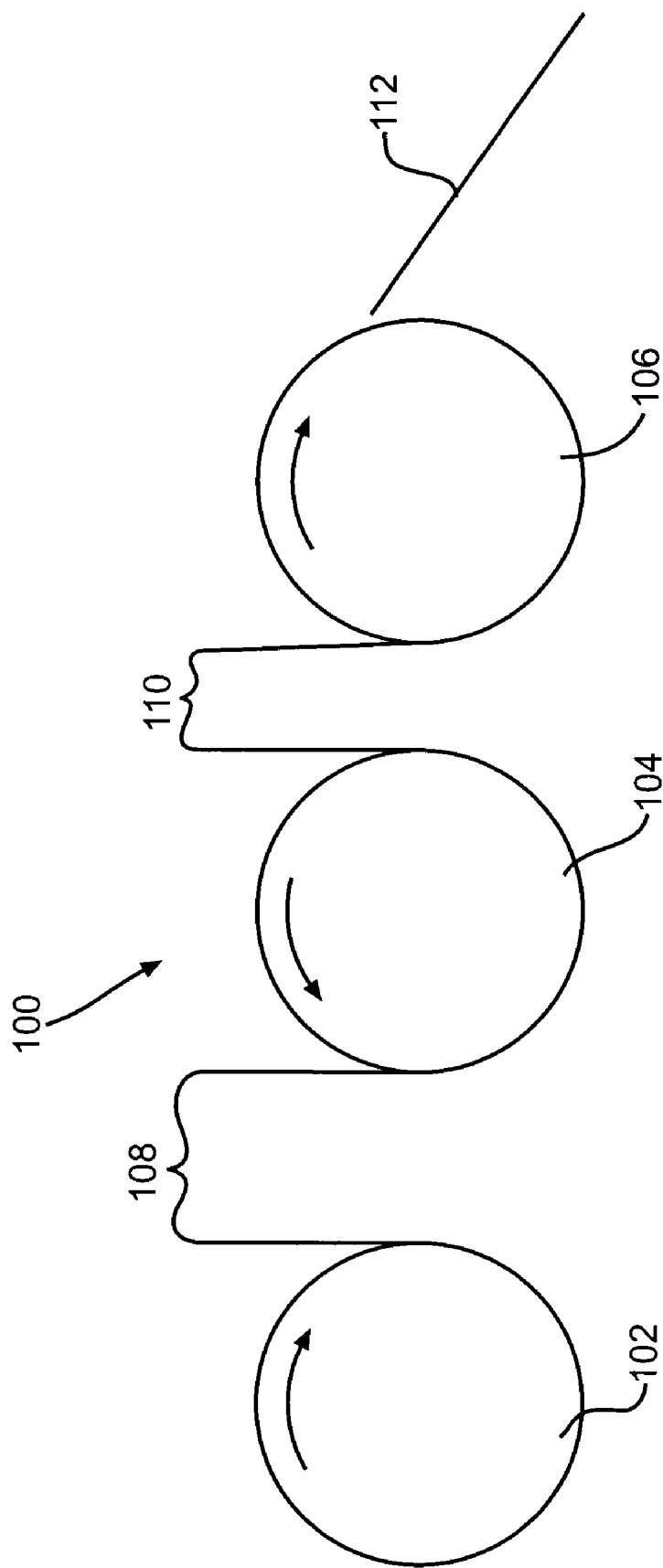
FIG. 3 is a schematic diagram of the 3-roll mill 100.

Once the correct amounts of silicone elastomer 50 and perlite particles 52 have been determined, the next step is to mix the perlite particles 52 into the silicone elastomer 50. The perlite particles 52 are mixed into the silicone elastomer 50 using a 2-roll mill, 1 arm or 2 arm mixer or equivalent piece of equipment so that the perlite particles 52 are dispersed into the silicone elastomer 50. The combined silicone elastomer 50 and perlite compound is then passed through a 3-roll mill 100, or high intensity mixer so that any of the perlite particles 52 which have agglomerated are separated into perlite particles 52 within a predetermined size range and evenly or uniformly dispersed throughout the silicone elastomer 50 (FIG. 3). The use of perlite particles 52 as the abrasive material in the prophylaxis cup 10 has necessitated a change in the processing of the compound to provide the prophylaxis cup 10. The perlite particles 52 form agglomerates and must be mixed or compounded into the silicone elastomer 50 using either a size reduction method or high intensity mixer. One (1) way of accomplishing this is to use a 3-roll mill 100. Another method would be to utilize one (1) of several types of high intensity internal mixers. This additional step ensures that any agglomeration of perlite particles 52 are separated sufficiently so that the resulting perlite particles 52 will be within the predetermined size range and will be evenly dispersed into the final molded prophylaxis cup 10. Evenly dispersing the perlite particles 52 throughout the prophylaxis cup 10 provides for even wear and uniform disintegration of the prophylaxis cup 10 during the use of the prophylaxis cup 10. In addition, providing a uniform starting particle size of the perlite particle 52 in the prophylaxis cup 10 produces optimal stain removal and polishing. In one (1) embodiment, the perlite particles 52 achieve an average particle size of between approximately 15 and 40 microns during the processing.

In one (1) embodiment using a 3-roll mill 100, the compound is passed through the 3-roll mill 100 at least twice to uniformly disperse the perlite particles 52 throughout the silicone elastomer 50. The three (3) rollers 102, 104 and 106 of the 3-roll mill 100 are rotating at different rates of speed so that a shearing effect is produced in the compound as the compound moves between the rollers 102, 104 and 106. The shearing action breaks down any agglomeration of perlite particles 52 to within the range of predetermined size and helps to disperse the perlite particles 52 uniformly throughout the silicone elastomer 50. In one (1) embodiment, the first roller 102 is the slowest and the last roller 106 is the fastest. In one (1) embodiment, the first roller 102 rotates at a speed of approximately 20 rpm, the second roller 104 rotates at a speed of approximately 30 rpm and the third roller 106 rotates at a speed of approximately 40 rpm. In one (1) embodiment, cheek plates are provided near each end of the rollers 102, 104 and 106, and act to funnel or guide the compound between the rollers 102, 104 and 106. An initial pass through the mill 100 can be done with the roll separation or "nip" between the first and second rollers 102 and 104 and the second and third rollers 104 and 106 set at approximately 120 microns. The second and subsequent passes through the 3-roll mill 100 are done with the first nip 108 between the first and second rollers 102 and 104 set at 120 microns and the second nip 110 between the second and third rollers 104 and 106 set at about 80 and 40 microns for the second and subsequent passes, respectively (FIG. 3). In one (1) embodiment for the initial or first pass, the first nip 108 or roll separation between the first and second rollers 102 and 104 is set at approximately 125 microns and the second nip 110 or roll separation between the second and third rollers 104 and 106 is set at approximately 100 microns. For the second pass, the first nip 108 is set at approximately 120 microns and the second nip 110 is set at approximately 50 microns. For the final or third pass, the first nip 108 is set at approximately 120 microns and the second nip 110 is set at approximately 25 microns. The mill 100 should be cleaned between each pass to ensure consistency of the compound. A scraper 112 is positioned adjacent the third roller 106 and acts to remove the compound from the third roller 106 and out of the 3-roll mill 100.

Once the compound is throughly mixed, the compound is ready for molding. The compound is weighed into amounts suitable for the mold being used. In one (1) embodiment, the mold is preheated to between about 260° F. and 340° F. (127° C. and 171° C.). The compound is loaded into the mold and the mold closed. The compound remains in the mold for between about 1 to 3 minutes. The mold is then opened and the prophylaxis cup or cups 10 are removed. The prophylaxis cups 10 are then post cured for approximately 3 hours at about 280° F. (138° C.) in a re-circulating oven with a minimum of 1.9 ft$^3$/minute of new air flow per pound of silicone prophylaxis cups 10 present in the oven. The prophylaxis cups 10 are inspected for deformities and discoloration and are de-flashed using a cryogenic de-flashing system. In one (1) embodiment, the mold is a compression mold and the prophylaxis cups 10 are formed using heat and the compression of the plates of the mold. In another embodiment, the prophylaxis cups 10 are formed using injection molding.

In one (1) embodiment, to deflash the prophylaxis cups 10, the prophylaxis cups 10 are frozen to between about −180° F. to −200° F. (−118° C. to −129° C.). In one (1) embodiment, the prophylaxis cups 10 are frozen by placing the prophylaxis cups 10 in Nitrogen vapor. While the prophylaxis cups 10 are frozen, the prophylaxis cups 10 are bombarded with objects to remove the flash. In one (1) embodiment, the objects are plastic bb's. In one (1) embodiment, the prophylaxis cups 10 are bombarded for between about 8 to 15 minutes, depending upon the amount of flash to be removed. Once the flash is removed, the prophylaxis cups 10 are warmed to room temperature. In one (1) embodiment, during the deflashing, the bombardment of the prophylaxis cups 10 removes the case hardened surface of the prophylaxis cup 10 caused by the molding process. The deflashing process produces a matte finish on the surface of the prophylaxis cup 10. The deflashing process alters the surface of the prophylaxis cup 10 so that the prophylaxis cup begins to disintegrate more quickly and the perlite particles 52 separate from the prophylaxis cup 10 more quickly upon contact with the teeth 20. For prophylaxis cups 10 having perlite particles 52 which are processed using this deflashing process, the prophylaxis cup 10 begins to disintegrate and the perlite particles 52 begin to separate from the prophylaxis cup 10 less than 10 seconds after initial rotational, in use contact of the prophylaxis cup 10 with the teeth 20. In one (1) embodiment, the prophylaxis cup 10 having perlite particles 52 begins to disintegrate and the perlite particles 52 begin to separate from the prophylaxis cup 10 about 5 seconds after initial rotational, in use contact of the prophylaxis cup 10 with the teeth 20.

The disposable prophylaxis cup 10 is intended to be mounted on a prophylaxis angle 150. One (1) method of mounting the prophylaxis cup 10 on the prophylaxis angle 150 is described in U.S. Pat. No. 5,334,020 to Eckert which is incorporated herein in its entirety by reference. However, it is understood that any well known means of mounting the prophylaxis cup 10 to the prophylaxis angle 150 can be used. The prophylaxis cup 10 can be used with a disposable prophylaxis angle or a non-disposable prophylaxis angle 150.

Figure 2:
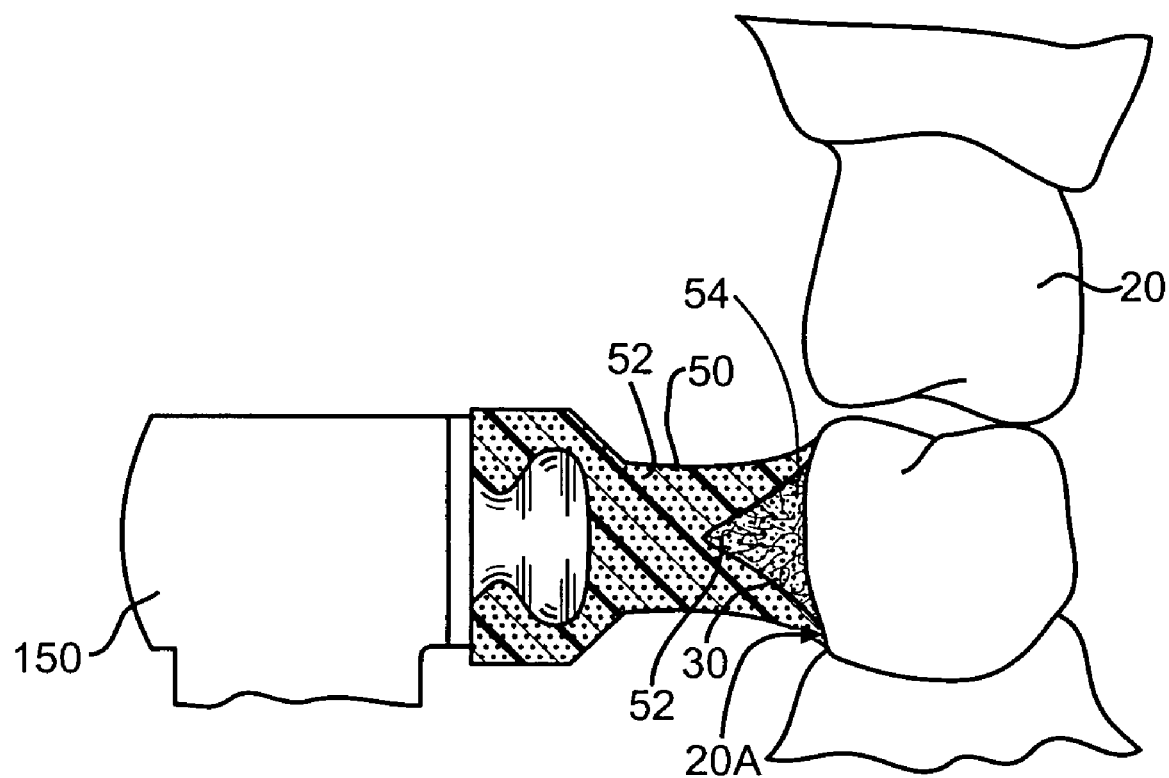
FIG. 2 is a side view showing the prophylaxis cup 10 in contact with a tooth 20 and showing the slurry 30 having the perlite particles 52 and the smaller perlite particles 54.

To use the prophylaxis cup 10 to clean and polish teeth 20, the prophylaxis cup 10 is positioned on the surface 20A of the tooth 20 (FIG. 2). In one (1) embodiment, initially the prophylaxis cup 10 is positioned on the surface 20A of the tooth 20 so that an axis of the prophylaxis cup 10 is perpendicular to the surface 20A of the tooth 20. The prophylaxis angle 150 is then activated so that the prophylaxis cup 10 rotates. The user then applies pressure on the tooth 20 so that the prophylaxis cup 10 deforms on the surface 20A of the tooth 20 so that the surface 20A of the tooth 20 contacts the inner surface of the prophylaxis cup 10. The prophylaxis cup 10 is moved along the teeth 20 so that the prophylaxis cup 10 cleans and polishes the surfaces 20A of each tooth 20 individually. During cleaning, the prophylaxis cup 10 may be positioned so that all sides of the prophylaxis cup 10 may be used to clean and polish the surfaces 20A of the tooth 20. In one (1) embodiment, the prophylaxis cup 10 is placed in contact with the tooth 20 and then the prophylaxis angle 150 is activated to rotate the prophylaxis cup 10. In another embodiment, the prophylaxis angle 150 is activated first so that the prophylaxis cup 10 is rotating when the prophylaxis cup 10 makes contact with the surface 20A of the tooth 20. As the prophylaxis cup 10 spins on the surface 20A of the tooth 20 under load, the prophylaxis cup 10 disintegrates and the perlite particles 52 adjacent to the surface 20A of the tooth 20 are liberated or separated from the prophylaxis cup 10. In one (1) embodiment, the prophylaxis cup 10 begins to disintegrate and the perlite particles 52 begin to separate from the prophylaxis cup 10 less than 10 seconds after the rotating prophylaxis cup 10 makes initial contact with the surface 20A of the tooth 20 under load during use. In one (1) embodiment, the prophylaxis cup 10 begins to disintegrate and the perlite particles 52 begin to separate from the prophylaxis cup 10 approximately 5 seconds after the rotating prophylaxis cup 10 makes initial contact with the surface 20A of the tooth 20 under load during use. The liberated perlite particles 52 mix with the moisture or saliva on the tooth 20 and form a slurry 30 between the prophylaxis cup 10 and the surface 20A of the tooth 20. The slurry 30 acts as a cleaning and polishing agent. As the prophylaxis cup 10 breaks down, the silicone elastomer 50 is also released and becomes part of the slurry 30. As the user continues to apply pressure on the prophylaxis cup 10 on the surface 20A of the tooth 20 and the prophylaxis cup 10 continues to rotate on the surface 20A of the tooth 20, the perlite particles 52 in the slurry 30 contact the surface 20A of the tooth 20 and remove heavier stains from the surface 20A of the tooth 20. The first stage of cleaning the teeth 20 involves the removal of stains from the teeth 20. The perlite particles 52 initially released from the prophylaxis cup 10 have a size between about 15 and 40 microns. As the perlite particles 52 in the slurry 30 continually contact the surface 20A of the tooth 20, the perlite particles 52 fracture or break down into smaller particles 54. The expanded perlite particles 52 are very fragile and easily break down upon contact with the enamel on the surface 20A of the teeth 20. The rotation of the prophylaxis cup 10 on the surface 20A of the teeth 20 under load causes the smaller perlite particles 54 to rub against the surface 20A of the teeth 20 producing a highly polished surface. This completes the second, polishing stage of cleaning. In one (1) embodiment during the polishing stage, the smaller perlite particles 54 have a size less than 15 microns. The prophylaxis cup 10 continues to disintegrate throughout the prophylaxis cleaning and polishing procedure. The uniform distribution of the perlite particles 52 throughout the prophylaxis cup 10 enables the prophylaxis cup 10 to continue to clean and polish throughout the entire prophylaxis procedure. In one (1) embodiment, a standard and prophylaxis cleaning procedure lasts between about 4 to 15 minutes. It is understood that a second cup 10 could be used for heavy duty prophylaxis cleaning and polishing procedures. Once the teeth 20 are cleaned and polished, the prophylaxis cup 10 is removed and the slurry 30 is evacuated from the mouth of the patient. However, it is understood that all the materials in the prophylaxis cup 10 are inert and are not harmful to a patient if swallowed.

It is intended that the foregoing description be only illustrative of the present invention and that the present invention be limited only by the hereinafter appended claims.

I claim:

1. A method for forming a prophylaxis cup which comprises the steps of:
    (a) mixing a silicone elastomer and perlite particles so that the perlite particles are evenly dispersed into the silicone elastomer to produce a compound;
    (b) passing the compound through a roll mill so that a shearing effect is produced as the compound moves between the rollers to achieve separation of any agglomerated perlite particles and to produce a uniform dispersion of the perlite particles having an average particle size between about 15 and 40 microns in the silicone elastomer;
    (c) loading the compound in the mold and closing the mold around the compound to form the prophylaxis cup with a case hardened surface;
    (d) removing the prophylaxis cup with the case hardened surface from the mold;
    (e) post curing the prophylaxis cup with the case hardened surface in a heated oven; and
    (f) deflashing the prophylaxis cup using a cryogenic deflashing system with bombarded objects to produce a matte finish on the cup wherein during the deflashing, the case hardened surface of the prophylaxis cup is removed so that during use of the prophylaxis cup, the prophylaxis cup begins to disintegrate and the perlite particles separate from the prophylaxis cup less than 10 seconds after initial, rotational contact with the teeth.

2. The method of claim 1 wherein in step (a), an amount of perlite particles is between about 30 and 36 percent by weight of the compound.

3. The method of claim 1 wherein further in step (f) for the deflashing, the prophylaxis cup is frozen to between about $-180°$ and $-200°$ F. ($-118°$ C. to $-129°$ C.) and bombarded with the objects for between about 8 to 15 minutes to remove the flash.

4. The method of claim 3 wherein the objects are spherical plastic BB.

5. The method of claim 4 wherein the perlite particles separate from the prophylaxis cup about 5 seconds after initial, rotational contact with the teeth.

6. The method of claim 1 wherein in step (c), the mold is preheated and wherein the prophylaxis cup is formed using compression of the compound in the mold.

7. The method of claim 1 wherein in step (e), the prophylaxis cup is post cured in the oven for approximately three (3) hours at a temperature of approximately 280° F. (138° C.).

8. The method of claim 1 wherein the silicon elastomer is a reaction product of a vinyl silicone reacted with platinum.

9. The process of claim 1 wherein the mill is three roll mill where each roll is a different rate of speed and wherein the compound moves between the rollers at least twice.

* * * * *